US006635026B1

(12) United States Patent
Béné

(10) Patent No.: US 6,635,026 B1
(45) Date of Patent: Oct. 21, 2003

(54) HAEMOFILTRATION MACHINE FOR INDEPENDENTLY CONTROLLING THE CONCENTRATION OF A LEAST TWO IONIC SUBSTANCES IN A PATIENT'S INTERNAL MEDIUM

(75) Inventor: Bernard Béné, Irigny (FR)

(73) Assignee: Hospal Industrie, Meyzieu (FR)

( * ) Notice: Subject to any disclaimer, the term of this patent is extended or adjusted under 35 U.S.C. 154(b) by 70 days.

(21) Appl. No.: 09/705,740

(22) Filed: Nov. 6, 2000

Related U.S. Application Data
(60) Provisional application No. 60/182,206, filed on Feb. 14, 2000.

(30) Foreign Application Priority Data

Nov. 8, 1999 (FR) .............................................. 99 14253

(51) Int. Cl.[7] ........................ A61M 35/00; B01D 63/00; C02F 1/44
(52) U.S. Cl. .................... 604/5.04; 604/6.09; 604/4.01; 604/6.06; 604/5.01; 210/646; 210/647; 210/650; 210/321.71; 210/321.72; 210/929
(58) Field of Search .............................. 604/4.01, 5.01, 604/5.02–5.04, 6.09, 6.11, 6.16; 422/44; 210/645.7, 650–52, 739, 741, 85, 87–88, 90, 97, 103, 194, 195.1–195.2, 321.6, 321.71–321.72, 321.75, 321.77, 321.84, 348, 416.1, 418, 950

(56) References Cited

U.S. PATENT DOCUMENTS

| | | | | |
|---|---|---|---|---|
| 5,366,630 A | * | 11/1994 | Chevallet | 210/138 |
| 5,476,592 A | | 12/1995 | Simard | 210/651 |
| 5,578,223 A | * | 11/1996 | Bene et al. | 210/117 |
| 5,651,893 A | * | 7/1997 | Kenley et al. | 210/195.1 |
| 5,808,181 A | * | 9/1998 | Wamsiedler et al. | 210/646 |
| 6,123,847 A | | 9/2000 | Bene | 210/646 |
| 6,325,774 B1 | * | 12/2001 | Bene et al. | 210/321.71 |
| 6,423,231 B1 | * | 7/2002 | Collins et al. | 210/143 |

FOREIGN PATENT DOCUMENTS

| | | |
|---|---|---|
| DE | 196 54 746 A | 7/1998 |
| EP | 0 622 087 | 4/1994 |
| EP | 0 898 975 A | 3/1999 |
| EP | 0 898 976 A | 3/1999 |
| FR | 2 791 574 | 10/2000 |

OTHER PUBLICATIONS

"Long–Term Morbidity: Hemofiltration vs. Hemodialysis," Quellhorst, E., et al., Nephrologisches Zentrum Niedersachsen, Hann Münden, Deutschland, 1995.

* cited by examiner

*Primary Examiner*—Angela D. Sykes
*Assistant Examiner*—Patricia Bianco
(74) *Attorney, Agent, or Firm*—Finnegan, Henderson, Farabow, Garrett & Dunner LLP

(57) ABSTRACT

A haemofiltration machine designed to work with a haemofilter comprises two compartments separated by a semipermeable membrane, one compartment having an inlet connected to a withdrawing tube for taking blood from the patient and an outlet connected to a blood return tube, the other having an outlet connected to a tube for removing used liquid. The machine itself comprises a solution generator for preparing a first injectable solution from at least one concentrated solution; a circulation pump for injecting the first solution at a flow rate of $Q_{pre}$ into the withdrawing tube; an infusion pump for injecting a patient with a second solution containing a ionic substance [A] with a fixed concentration $[A]_{post}$ different from its concentration $[A]_{pre}$ in the first solution; and a control unit for determining an infusion flow rate Q(post) for the second solution such that the concentration of the ionic substance [A] inside the patient tends towards a required concentration $[A]_{des}$, as a function of $[A]_{post}$, $[A]_{des}$, $Q_{pre}$, and the blood flow rate $Q_B$.

20 Claims, 1 Drawing Sheet

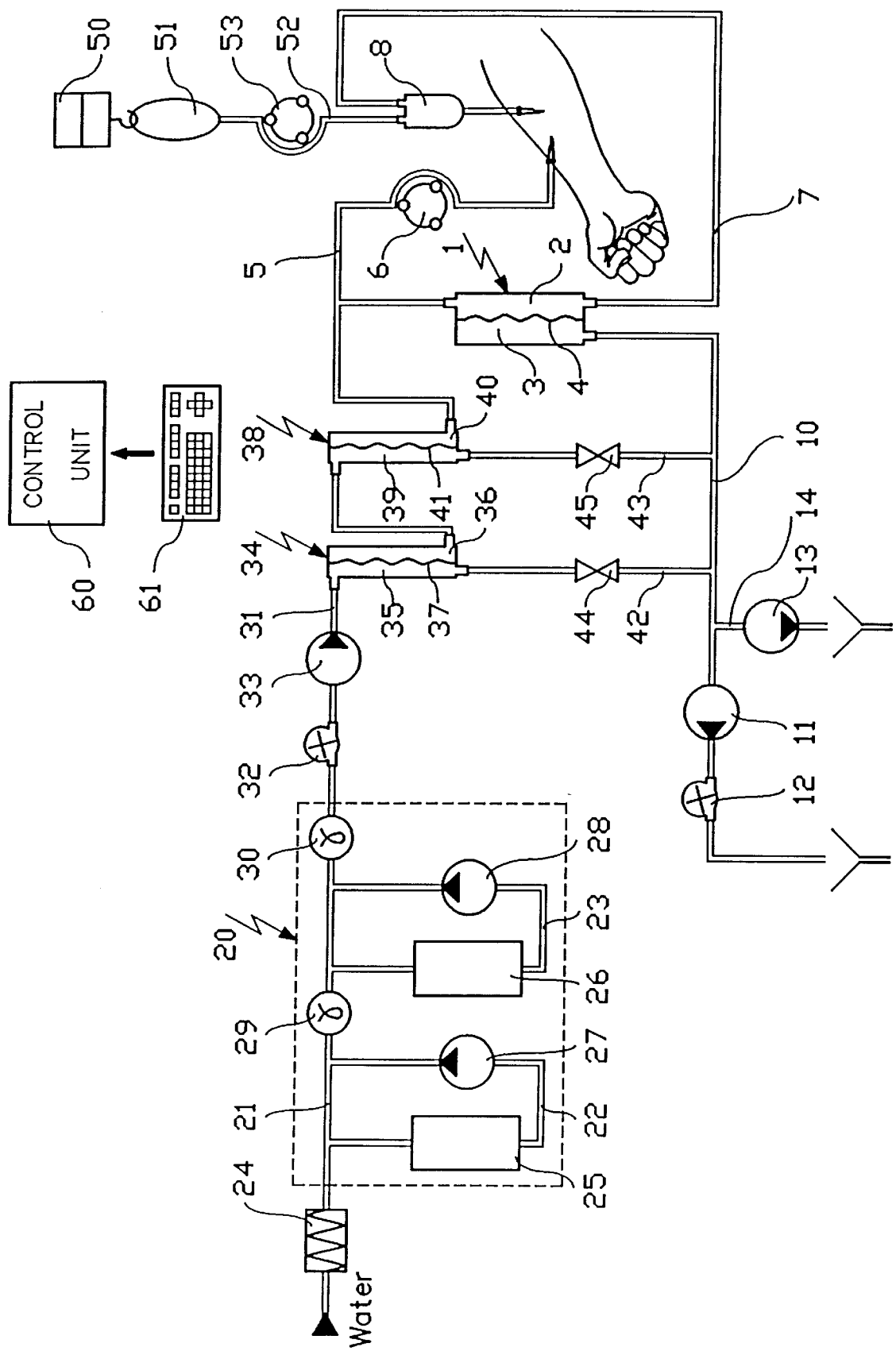

HAEMOFILTRATION MACHINE FOR INDEPENDENTLY CONTROLLING THE CONCENTRATION OF A LEAST TWO IONIC SUBSTANCES IN A PATIENT'S INTERNAL MEDIUM

CROSS REFERENCE TO RELATED APPLICATIONS

This application claims the right to priority based on U.S. Provisional Patent Application No. 60/182,206, filed on Feb. 14, 2000.

DESCRIPTION OF THE INVENTION

1. Field of the Invention

The present invention relates to a haemofiltration machine for independently controlling the concentration of at least two ionic substances in a patient's internal medium.

2. Background of the Invention

The present invention relates to a haemofiltration machine for independently controlling the concentration of at least two ionic substances in a patient's internal medium.

The kidneys fulfil many functions, among which are the removal of water, the excretion of catabolites (or metabolic waste, such as urea and creatinine), the regulation of the concentration of ionic substances in the blood (sodium, potassium, magnesium, calcium, bicarbonates, phosphates and chlorides) and the regulation of the acid-base equilibrium of the internal medium, which is obtained in particular by removing weak acids (phosphates, monosodium acids) and by the production of ammonium salts.

In individuals who have lost the use of their kidneys, since these excretory and regulatory mechanisms no longer work, the internal medium becomes loaded with water and metabolic waste and has an excess of certain ionic substances (in particular sodium), as well as, in general, exhibiting acidosis, with the pH of the blood plasma shifting towards 7 (the blood pH normally varies within a narrow range of between 7.35 and 7.45).

To overcome the dysfunction of the kidneys, use is conventionally made either of dialysis or of haemofiltration, which are blood treatments administered by means of an exchanger with a semi-permeable membrane (haemodialysis machine/haemofilter) which is linked to the patient via an extracorporeal blood circulation circuit.

Dialysis consists in circulating, on either side of the exchanger membrane, the patient's blood and a dialysis liquid comprising the main ionic substances of the blood, in concentrations close to those of the blood of a healthy individual. Moreover, a given volume of plasmatic water corresponding to the weight that the patient should lose during each dialysis session is made to flow by ultrafiltration through the membrane into the dialysis liquid compartment. The ultrafiltration results from a difference in pressure maintained between the two compartments of the exchanger delimited by the membrane.

The blood treatment which is carried out in the exchanger results from the diffusional transfer, across the membrane, of molecules of the same substance (ionic substances, metabolic waste) which are at different concentrations on either side of the membrane, the molecules migrating from the liquid in which they are at higher concentration to the liquid in which they are at lower concentration.

In a conventional dialysis machine, the dialysis liquid is prepared by means of a measured mixture of water and of two concentrated solutions, a first concentrated solution containing sodium chloride and sodium bicarbonate and the second concentrated solution containing calcium, potassium and magnesium chlorides as well as acetic acid. The role of the acetic acid is to limit the formation of calcium and magnesium carbonate precipitates which form unwanted deposits in the hydraulic circuit of the dialysis machine. Other dialysis devices have been proposed, in particular in documents EP 0 898 975 and EP 0 898 976, in which the dialysis liquid used contains no calcium or magnesium (as the respective bicarbonates) and in which a sodium bicarbonate solution (or a calcium or magnesium chloride solution, respectively) is infused into the patient. Irrespective of the type of dialysis administered, at the usual flow rate of dialysis liquid, i.e., 500 ml/min, 120 liters of dialysis liquid are prepared and used in the course of a four-hour dialysis session.

Haemofiltration consists in extracting from the blood circulating in the exchanger, by ultrafiltration, a large volume (up to thirty liters in the course of a four-hour session) of plasmatic water which is partially replaced by means of a simultaneous infusion of a sterile replacement liquid.

The blood treatment which is carried out in the exchanger results here from the convective transfer of molecules (ionic substances, metabolic waste) which are entrained by the plasmatic water which filters through the membrane under the effect of the pressure difference created between the two compartments of the exchanger.

The electrolyte composition of the replacement liquid used in haemofiltration is identical to that of a dialysis liquid. This liquid can be manufactured and packaged by a pharmaceutical laboratory in the form of two containers for two sterile liquids to be mixed together just before use, one of the containers containing all the bicarbonate and the other container containing all the calcium and magnesium. This replacement liquid can also be prepared at the time of use by filtration of a dialysis liquid, as is described in particular in document EP 0 622 087, the subject of which is a haemodiafiltration machine (combination of the two treatments defined above): in this machine, some of the dialysis liquid produced by a dialysis liquid generator is injected, after filtration, into the blood return tube of the extracorporeal circuit, while the rest of the dialysis liquid is circulated in the exchanger.

Despite its efficacy and its acknowledged superiority over dialysis in therapeutic terms (see, in particular, *Long-term morbidity: Hemofiltration vs. Hemodialysis*, by E. Quellhorst, U. Hildebrand, A. Solf, in Contrib. Nephrol. Basle, Karger, 1995, vol 113, pp. 110–119), the haemofiltration suffers from two limitations: a first limitation is associated with the cost of the treatment when the replacement liquid used is purchased ready-to-use. Since these sterile solutions packaged in split containers are expensive, the tendency is to limit the treatment administered to an exchange of liquids not exceeding thirty liters (i.e., a quarter as much as the volume of treatment liquid used during a dialysis session). The second limitation is that, even with a machine such as the one described in document EP 0 622 087 mentioned above, which provides replacement liquid at reduced cost, the exchange flow rate is limited since the ultrafiltration flow rate cannot be set at much more than a third of the flow rate of the blood in the extracorporeal circuit.

BRIEF SUMMARY OF THE INVENTION

In the light of the foregoing considerations, one aim of the invention is to produce a system for treating renal insufficiency which makes it possible to carry out a haemofiltration session in the course of which very large volumes of liquid can be exchanged, without this haemofiltration session being any longer or any more expensive than a conventional dialysis session, and also without it displaying the known drawbacks relating to the preparation of an unstable treatment liquid.

In accordance with the invention, this aim is achieved by means of a haemofiltration machine designed to cooperate with a haemofilter having a first compartment and a second compartment separated by a semi-permeable membrane, the first compartment having an inlet which can be connected to a blood withdrawing tube and an outlet which can be connected to a blood return tube, and the second compartment having an outlet which can be connected to a spent liquid evacuation tube. This haemofiltration machine comprises means for preparing a first injectable solution from at least one concentrated solution; means for injecting, at an injection flow rate $Q_{pre}$, the first solution into the blood withdrawing tube; means for infusing into the blood return tube a second solution containing at least one ionic substance A having a given concentration $[A]_{post}$ which is different from the concentration $[A]_{pre}$ of this substance A in the first solution; means for determining an infusion flow rate $Q_{post}$ of the second solution in order for the concentration of the substance A in the patient's internal medium to tend towards a desired concentration $[A]_{des}$, as a function of the concentration $[A]_{post}$ of the substance A in the second solution, the desired concentration $[A]_{des}$, the injection flow rate $Q_{pre}$ of the first solution and the blood flow rate $Q_B$; and control means for governing the infusion means such that the flow rate of the second solution is substantially equal to the determined flow rate $Q_{post}$.

The invention makes it possible to achieve the pursued aim since, as the first solution is injected upstream of the exchanger, the blood which penetrates into the exchanger is diluted such that the proportion of this mixture which can be ultrafiltered is very much higher than the admissible proportion when the blood is not diluted. Consequently, it is possible with this machine to envisage administering a treatment in the course of which fifty to eighty liters of treatment liquid are exchanged against the same volume of plasmatic water. Moreover, dilution of the blood reduces the drawbacks associated with the viscosity of the total blood, i.e., the resistance to flow and the hindrance to transfers, and it reduces the risks of clotting in the exchanger since the concentration of clotting factors therein is reduced. The ultrafiltration of a diluted blood is also less traumatic for the components present in the blood than the ultrafiltration of undiluted blood.

This system also has the advantage in that the respective concentrations of at least two ionic substances forming part of the composition of a replacement liquid can be controlled independently of each other, which is often desirable at least for sodium, potassium or bicarbonate.

According to one characteristic of the invention, the substance A is absent from the first solution and the means for determining the infusion flow rate $Q_{post}$ comprise calculation means for calculating the infusion flow rate $Q_{post}$ according to the formula:

$$Q_{post} = \frac{[A]_{des} \times Q_B \times Q_{pre}}{[A]_{post} \times Q_B + [A]_{post} \times Q_{pre} - [A]_{des} \times Q_B} \quad (1)$$

According to one embodiment of the invention, the first or second solution contains bicarbonate and contains no magnesium or calcium, while the other solution contains magnesium and calcium and contains no bicarbonate.

By means of separating the bicarbonate, on the one hand, and the magnesium and calcium, on the other hand, it is unnecessary to add acetic acid to either of the solutions to avoid the formation of unwanted precipitates, and this has obvious advantages as regards the devices used for preparing the solutions, which are not exposed to corrosion due to the action of an acid, or to encrustation due to carbonate-based deposits. Moreover, the absence of acid from the first solution is desirable in therapeutic terms since it appears that the dilution of blood with a liquid whose pH is less than that of blood is one of the co-factors of certain hypersensitivity reactions.

Another advantage of the invention lies in the possibility of continuously determining and adjusting the flow rate of the second solution, in particular when this solution contains all the calcium, magnesium and potassium infused into the patient. Specifically, it is known that an excess, much like a deficit, of potassium, calcium or magnesium in the blood can give rise to serious disorders in the patient, in particular heart disorders. Now, ultrafiltration of the blood brings about the convective removal of some of the ionic substances in the diluted blood which circulates in the exchanger, and this convective loss varies as a function of the parameters of the treatment which are modified in the course of treatment, such as the flow rate of the first solution and the flow rate of the blood. By virtue of the means, possessed by the haemofiltration machine according to the invention, for determining the flow rate of the second solution, it is possible to continuously compensate for the variable convective losses which arise in the exchanger.

The infusion, downstream of the exchanger or directly in the patient, of a second solution containing all the calcium infused into the patient, also has a further advantage resulting from the depletion of calcium from the diluted blood in the exchanger: it is known that ionic calcium is involved in the cascade of reactions constituting the blood-clotting process. Massive depletion of calcium from the blood in the exchanger thus partially inhibits the clotting process, thereby making it possible to reduce the amount of anticoagulant injected into the extracorporeal blood circulation circuit to prevent the blood from clotting therein.

Other characteristics and advantages of the invention will become more apparent on reading the description which follows.

BRIEF DESCRIPTION OF THE DRAWINGS

Reference will be made to the single FIGURE attached, which diagrammatically represents a haemofiltration machine according to the invention.

DETAILED DESCRIPTION OF THE INVENTION

The haemofiltration machine represented in the FIGURE comprises an exchanger 1 with two compartments 2, 3 separated by a semi-permeable membrane 4. A first compartment 2 has an inlet connected to a blood withdrawing tube 5 (referred to as the "arterial" tube) on which is placed a circulation pump 6, and an outlet connected to a blood return tube 7 (referred to as the "venous" tube) on which is interposed a bubble trap 8. The first compartment 2 of the exchanger 1, the blood withdrawing tube 5 and the blood return tube 7 constitute the circuit for the extracorporeal circulation of blood by the machine.

The second compartment 3 of the exchanger 1 has an outlet connected to a spent liquid evacuation tube 10

(ultrafiltrate), the free end of which is arranged to be connected to the drain. A first pump 11 and a flow meter 12 are provided on this tube 10, in the direction of circulation of the liquid. A second pump 13 is provided on an extraction tube 14 connected to the evacuation tube 10, upstream of the first pump 11.

The haemofiltration machine according to the invention also comprises a first device for injecting a first solution into the extracorporeal blood circulation circuit upstream of the exchanger 1. This injection device comprises a generator 20 of liquid for medical use which is capable of producing a solution of given composition by diluting at least one concentrated solution. The generator 20 represented consists of a main tube 21 to which are connected in series two secondary branch tubes 22, 23. The upstream end of the main tube 21 is arranged so as to be connected to a source of running water which can be brought to the desired temperature by means of a heating member 24. Each secondary tube 22 (23) comprises connecting means for mounting a cartridge 25 (26) containing a salt in the form of granules. A pump 27 (28) is provided on each secondary tube 22 (23) downstream of the corresponding cartridge 25 (26) in order to circulate therein the liquid from the main tube. Each pump 27 (28) is governed as a function of the comparison between 1) a set conductivity value for the mixture of liquids forming at the junction of the main line 21 and of the downstream end of the secondary line 22 (23), and 2) the conductivity value of this mixture measured by means of a conductivity probe 29 (30) provided on the main tube 21 immediately downstream of the junction between the main tube 21 and the downstream end of the secondary tube 22 (23).

The solution generator 20 is connected to the extracorporeal blood circulation circuit by means of an injection tube 31 which has one end connected to the main tube 21 of the generator 20 and its other end connected to the blood withdrawing tube 5, downstream of the blood pump 6. This injection tube 31 is provided, in the direction of circulation of the liquid, with a flow meter 32, a circulation pump 33, a first filter 34 which has two chambers 35, 36 separated by an ultrafiltration membrane 37 and a second filter 38 which has two chambers 39, 40 separated by an ultrafiltration membrane 41. The chamber 35 (39) of each of the two filters 34, 38 into which the solution to be filtered is introduced has an outlet connected to the evacuation tube 10 via a maintenance tube 42 (43) on which is provided a valve 44 (45).

The haemofiltration machine according to the invention also comprises a second device for infusing a second solution into the extracorporeal blood circulation circuit, downstream of the exchanger 1. This infusion device comprises a balance 50 provided for weighing a bag 51 of solution which is connected to the blood return tube 7 via an infusion tube 52 on which is provided a pump 53. The balance 50 is used to govern the pump 51 such that the flow rate of the infusion liquid is equal to a set flow rate.

The haemofiltration system represented in the FIGURE also comprises a calculation and control unit 60. This unit is connected to an alphanumeric keyboard 61 by means of which an operator can give it instructions, such as various set values. Moreover, it receives information emitted by the members for measuring the system, such as the flow meters 12, 32 the conductivity probes 29, 30 and the balance 50. It governs, as a function of the instructions received and the modes of operation and the algorithms programmed, the members driving the system, such as the pumps 6, 11, 13, 27, 28, 33, 53 and the valves 44, 45.

In the embodiment of the invention represented in the FIGURE, the cartridge 25 contains only sodium bicarbonate, the cartridge 26 contains only sodium chloride, and the bag 51 of infusion liquid contains a solution of potassium, magnesium and calcium chloride. The bag 51 optionally also contains sodium.

The haemofiltration machine which has just been described operates in the following way.

An operator inputs into the control unit 60, via the keyboard 61, set values corresponding to the various parameters of the treatment (prescription), namely the blood flow rate $Q_B$, the flow rate of the first solution $Q_{pre}$, the total weight loss WL (amount of plasmatic water to be removed from the patient by ultrafiltration), the total time T of the session, the bicarbonate concentration $[HCO_3^-]_{pre}$ of the first solution, the sodium concentration $[Na^+]_{pre}$ of the first solution, the potassium concentration $[K^+]_{post}$ of the second solution and the potassium concentration $[K^+]_{des}$ towards which the concentration of the patient's internal medium must tend.

In accordance with the invention, the control and calculation unit 60 then calculates the flow rate $Q_{post}$ of the second solution which is required to compensate for the convective losses which arise in the exchanger (in particular the losses of potassium) and, possibly, to correct the potassium concentration in the patient's internal medium and to make it tend towards the desired concentration $[K^+]_{des}$. The formula used to carry out this calculation, which is stored in a memory of the control unit 60, is as follows:

$$Q_{post} = \frac{[K^+]_{des} \times Q_B \times Q_{pre}}{[K^+]_{post} \times Q_B + [K^+]_{post} \times Q_{pre} - [K^+]_{des} \times Q_B}$$

In accordance with the invention, the control and calculation unit 60 is programmed to recalculate the flow rate $Q_{post}$ of the second solution each time one of the parameters of the treatment is modified, in particular the blood flow rate $Q_B$ and the flow rate of the first solution $Q_{pre}$.

After a sodium bicarbonate cartridge 25 and a sodium chloride cartridge 26 have been connected to the corresponding tubes 22, 23 of the solution generator 20, the main tube 21 is connected to a source of running water and the pumps 27, 28, 33, 11 are switched on. The valves 44, 45 provided on the maintenance tubes 42, 43 are opened, such that, in an initial operating phase of the machine, the liquid produced by the solution generator 20 is sent to the drain. The pumps 27 and 28 are governed by the control unit 60 such that the bicarbonate concentration and the sodium concentration in the first solution are equal to the corresponding set values $[HCO_3^-]_{pre}$ and $[Na^+]_{pre}$. The pump 33 for injecting the first solution is governed by the control unit 60 such that its flow rate is equal to the set flow rate $Q_{pre}$ (for example 300 ml/min.) and the flow rate of the pump 11 for circulating spent liquid is adjusted by the control unit 60 such that the flow rates measured by the flow meters 32, 12 are equal. When the first solution has the desired concentration of sodium and bicarbonate, the valve 44 is closed, while the valve 45 is left open for a few moments until the first chamber of the second filter 38 has been rinsed and filled with solution, as well as the second maintenance tube 43. After closing the valve 45, the first solution is filtered a second time and this solution, which is injectable thereafter, is used to rinse and fill the extracorporeal blood circulation circuit (blood withdrawing tube 5, first compartment 2 of the exchanger 1, return tube 7).

When the priming (i.e., the rinsing and filling) of the injection circuit with the first solution and the priming of the blood circuit are complete, the blood circuit is connected to the patient and the actual treatment can begin: the pumps 27, 28 of the solution generator 20, and the solution injection pump 33 and the spent liquid circulation pump 11 continue to operate as during the priming of the circuit, while the blood pump 6, the extraction pump 13 and the infusion pump 53 are switched on. The blood pump 6 is adjusted to the set flow rate $Q_B$ (for example 300 ml/min.) and the extraction pump 13 is adjusted to a flow rate calculated by the control unit 60 and equal to the sum of the rate of weight loss WL/T and the infusion flow rate $Q_{post}$ of the second solution. In accordance with the invention, the infusion pump 53 is adjusted to the flow rate $Q_{post}$ calculated by the control unit as mentioned above.

EXAMPLE

The parameters of a haemofiltration treatment administered by the machine according to the invention are defined as follows:

blood flow rate $Q_B$ =300 ml/min.

flow rate of the first solution =300 ml/min.

composition of the first solution:
If the objective to be achieved, in terms of sodium concentration $[Na^+]_{des}$ in the internal medium is 141 millimol, then the sodium concentration of the first solution is adjusted to $[Na^+]_{pre}$=147 millimol/liter.
If the objective to be achieved, in terms of bicarbonate concentration $[HCO_3^-]_{des}$ in the internal medium is 33.5 millimol, then the bicarbonate concentration of the first solution is adjusted to $[HCO_3^-]_{pre}$=35 millimol/liter.

composition of the second solution: an infusion liquid is chosen which is isotonic with the blood and in which the relative proportions of the ions are equal to the desired relative proportions of these same ions in the patient's internal medium. That is to say, for example, the infusion liquid of the following composition:
$[K^+]$=60 millimol/liter
$[Mg^{++}]$=15 millimol/liter
$[Ca^{++}]$=45 millimol/liter
$[Cl^-]$=180 millimol/liter flow rate of the second solution: if the objective to be achieved, in terms of potassium concentration $[K^+]_{des}$ in the internal medium is 2.5 millimol, then the flow rate of the infusion pump for the second solution must be adjusted to 6.4 ml/min., by applying equation (1).

In the preceding example, the objective to be achieved was defined in terms of potassium concentration $[K^+]_{des}$ in the internal medium. It goes without saying that when the calcium or magnesium is considered as the critical substance for a given patient, the infusion pump 53 will be adjusted as a function of an objective defined in terms of the desired concentration of calcium $[Ca^{++}]_{des}$ or magnesium $[Mg^{++}]_{des}$ in the patient's internal medium.

Moreover, in the embodiment of the invention which has been described above, it is only possible to make the patient's internal medium tend towards a given concentration for one of the ionic substances contained in the second solution. If it is desired to target several objectives in terms of concentration of ionic substances contained in the second solution, it suffices to use several bags of infusion liquid each containing a single ionic substance to be dosed and to provide an equal number thereof of infusion means (balance and pump). It is also possible to use only a single balance, on which the various bags are suspended, and only a single pump associated with distribution means for connecting in turn, according to a given time sequence, each bag and the extracorporeal blood circulation circuit.

The invention which has just been described is capable of being varied, in particular as regards the composition of the first solution and of the second solution, and the preparation of the first injectable solution.

Provided that the main ionic substances of the blood are present in one and/or the other solution, the ionic composition of the first solution and of the second solution can be chosen very freely. Preferably, for the reasons which have been outlined above, the ionic substances which form carbonate-based precipitates when the pH of the solution in which they are present is above about 7.5 are separated and form part of the composition of only one or other of the two solutions.

Thus, the second solution can contain only sodium bicarbonate and the first solution can contain the main ionic substances of the blood except for bicarbonate (i.e., chlorine, sodium, magnesium, calcium, potassium). In this case, the first solution can be prepared from a single concentrated liquid solution, and the solution generator of the machine in this case comprises dilution means for diluting a single concentrated solution (a pump, adjusted by means of a conductivity probe, to inject the concentrated solution into a main tube connected to a source of running water). With such an arrangement, it is possible to make the patient's internal medium tend towards two prescription values, a sodium concentration $[Na^+]_{des}$ and a bicarbonate concentration $[HCO_3^-]_{des}$.

The first solution can also be prepared from two concentrated liquid solutions containing the same ionic substances in the same concentrations, except for potassium whose concentration in the two concentrated solutions is different. In this case, the solution generator for the haemofiltration machine is similar to that which has been described above in relation to the attached FIGURE. By carefully governing the two pumps used to inject the two concentrated solutions into the main tube of the solution generator, the potassium concentration in the first solution can be adjusted according to the needs of each particular patient. With such an arrangement, it is possible to make the patient's internal medium tend towards three prescription values, a sodium concentration $[Na^+]_{des}$, a potassium concentration $[K^+]_{des}$ (by means of the first solution) and a bicarbonate concentration $[HCO_3^-]_{des}$ (by means of the second solution).

When the substance A, whose concentration in the patient's internal medium it is desired to make tend towards a desired concentration $[A]_{des}$, is present not only in the second solution but in both the first solution and in the second solution (for example potassium), this should be taken into account when calculating the infusion flow rate $Q_{post}$ of the second solution. The formula with which the control and calculation unit 60 then calculates the infusion flow rate $Q_{post}$ of the second solution is as follows:

$$[A]_{des} \times (Q_{pre}+Q_{post}) \times Q_B/(Q_B+Q_{pre}) = ([A]_{pre} \times Q_{pre}) + ([A]_{post} \times Q_{post}) \quad (2)$$

In the embodiment which has been described above, the first solution prepared by the solution generator 20 is made injectable by filtering it through the two filters 34 and 38. This first solution might naturally be made injectable by other means, in particular by a heat-sterilization installation as described in document FR 99/04207.

What is claimed is:

1. Haemofiltration machine designed to cooperate with a haemofilter having a first compartment and a second compartment separated by a semi-permeable membrane, the first compartment having an inlet which can be connected to a blood withdrawing tube and an outlet which can be connected to a blood return tube, and the second compartment having an outlet which can be connected to a spent liquid evacuation tube, the haemofiltration machine comprising:

means for preparing a first injectable solution from at least one concentrated solution;

means for injecting, at an injection flow rate $Q_{pre}$, the first solution into the blood withdrawing tube;

means for infusing into the blood return tube a second solution containing at least one ionic substance A having a given concentration $[A]_{post}$ which is different from the concentration $[A]_{pre}$ of this substance A in the first solution;

means for determining an infusion flow rate $Q_{post}$ of the second solution in order for the concentration of the substance A in the patient's internal medium to tend towards a desired concentration $[A]_{des}$, as a function of the concentration $[A]_{post}$ of the substance A in the second solution, the desired concentration $[A]_{des}$, the injection flow rate $Q_{pre}$ of the first solution and the blood flow rate $Q_B$; and control means for governing the infusion means such that the flow rate of the second solution is substantially equal to the determined flow rate $Q_{post}$.

2. Machine according to claim 1, wherein the means for preparing the first injectable solution comprise:

first dilution means for diluting a first concentrated sodium chloride solution;

second dilution means for diluting a second concentrated sodium bicarbonate solution; and means for adjusting the first and second dilution means such that the first solution has a given sodium concentration and a given bicarbonate concentration.

3. Machine according to claim 2, wherein the means for preparing the first injectable solution comprise means for producing the first concentrated solution from sodium chloride in the form of powder or granules, and means for producing the second concentrated solution from sodium bicarbonate in the form of powder or granules.

4. Machine according to claim 3, wherein the second solution comprises calcium, potassium, and magnesium and the substance A is one of calcium, potassium, and magnesium.

5. Machine according to claim 2, wherein the second solution comprises calcium, potassium, and magnesium and the substance A is one of calcium, potassium, and magnesium.

6. Machine according to claim 1, wherein the means for preparing the first injectable solution comprise:

dilution means for diluting a concentrated solution of sodium, calcium, potassium and magnesium chlorides; and means for adjusting the dilution means such that the first solution has a given sodium concentration.

7. Machine according to claim 6, wherein the second solution comprises sodium bicarbonate and in that substance A is bicarbonate.

8. Machine according to claim 1, wherein the means for preparing the first injectable solution comprise:

first dilution means for diluting a first concentrated solution of sodium, calcium, potassium and magnesium chlorides, in which the potassium is at a first concentration;

second dilution means for diluting a second concentrated solution of sodium, calcium, potassium and magnesium chlorides, in which the potassium is at a second concentration; and means for adjusting the first and second dilution means such that the potassium is at a third given concentration in the first solution.

9. Machine according to claim 8, wherein the second solution comprises sodium bicarbonate and in that substance A is bicarbonate.

10. Machine according to claim 1, wherein the substance A is absent from the first solution and the means for determining the infusion flow rate $Q_{post}$ comprise calculation means for calculating the infusion flow rate $Q_{post}$ according to the formula:

$$Q_{post} = \frac{[A]_{des} \times Q_B \times Q_{pre}}{[A]_{post} \times Q_B + [A]_{post} \times Q_{pre} - [A]_{des} \times Q_B}.$$

11. Machine according to claim 1, wherein the means for preparing the first injectable solution comprise means for filtering the first solution.

12. Machine according to claim 1, wherein the first or second solution contains bicarbonate and contains no magnesium or calcium, while the other solution contains magnesium and calcium and contains no bicarbonate.

13. A hemofiltration machine, comprising:

a hemofilter having a first compartment and a second compartment separated by a semi-permeable membrane, the first compartment having an inlet and an outlet, the second compartment having an outlet configured to be connected to a spent liquid evacuation tube;

a blood withdrawing tube coupled to the inlet of the first compartment, the blood withdrawing tube being configured to direct blood flow from a patient to the hemofilter;

a blood return tube coupled to the outlet of the first compartment, the blood return tube being configured to direct the blood flow from the hemofilter to the patient;

a solution generator configured to prepare a first solution from at least one concentrated solution;

a first infusion assembly configured to inject the first solution into the blood withdrawing tube at a first infusion flow rate;

a second infusion assembly configured to inject a second solution into the blood flow, the second solution containing at least one ionic substance having a given concentration that is different from a concentration of said at least one ionic substance in the first solution; and a controller configured to determine an infusion flow rate of the second solution in order for the concentration of the substance A in the patient's internal medium to tend towards a desired concentration, the infusion flow rate of the second solution being a function of the concentration of said at least one ionic substance in the second solution, the desired concentration, the infusion flow rate of the first solution, and blood flow rate.

14. The machine of claim 13, wherein the controller is configured to govern the first and second infusion assemblies such that the infusion flow rate of the second solution is substantially equal to the determined infusion flow rate of the second solution.

15. The machine of claim 13, wherein the solution generator is configured to dilute at least one concentrated solution to prepare the first solution.

16. The machine of claim 13, wherein the second infusion assembly is configured to inject the second solution into the blood return tube.

17. The machine of claim 13, wherein the second infusion assembly is configured to inject the second solution directly into the patient's blood.

18. The machine of claim 13, wherein the first infusion assembly comprises:

a first diluting assembly configured to dilute a first concentrated sodium chloride solution;

a second diluting assembly configured to dilute a second concentrated sodium bicarbonate solution, the first infusion assembly being configured to adjust the first and second diluting assemblies such that the first solution has a given sodium concentration and a given bicarbonate concentration, and wherein the second solution comprises calcium, potassium, and magnesium and said at least one ionic substance is one of calcium, potassium, and magnesium.

19. Haemofiltration machine designed to cooperate with a haemofilter having a first compartment and a second compartment separated by a semi-permeable membrane, the first compartment having an inlet which can be connected to a blood withdrawing tube and an outlet which can be connected to a blood return tube, and the second compartment having an outlet which can be connected to a spent liquid evacuation tube, the haemofiltration machine comprising:

means for preparing a first injectable solution from at least one concentrated solution;

means for injecting, at an injection flow rate $Q_{pre}$, the first solution into the blood withdrawing tube;

means for infusing directly into a patient's blood a second solution containing at least one ionic substance A having a given concentration $[A]_{post}$ which is different from the concentration $[A]_{pre}$ of this substance A in the first solution;

means for determining an infusion flow rate $Q_{post}$ of the second solution in order for the concentration of the substance A in the patient's internal medium to tend towards a desired concentration $[A]_{des}$, as a function of the concentration $[A]_{post}$ of the substance A in the second solution, the desired concentration $[A]_{des}$, the injection flow rate $Q_{pre}$ of the first solution and the blood flow rate $Q_B$; and control means for governing the infusion means such that the flow rate of the second solution is substantially equal to the determined flow rate $Q_{post}$.

20. Haemofiltration machine designed to cooperate with a haemofilter having a first compartment and a second compartment separated by a semi-permeable membrane, the first compartment having an inlet which can be connected to a blood withdrawing tube and an outlet which can be connected to a blood return tube, and the second compartment having an outlet which can be connected to a spent liquid evacuation tube, the haemofiltration machine comprising:

means for preparing a first injectable solution from at least one concentrated solution;

means for injecting, at an injection flow rate $Q_{pre}$, the first solution into the blood withdrawing tube;

means for infusing into the a patient a second solution containing at least one ionic substance A having a given concentration $[A]_{post}$ which is different from the concentration $[A]_{pre}$ of this substance A in the first solution;

means for determining an infusion flow rate $Q_{post}$ of the second solution in order for the concentration of the substance A in the patient's internal medium to tend towards a desired concentration $[A]_{des}$, as a function of the concentration $[A]_{post}$ of the substance A in the second solution, the desired concentration $[A]_{des}$, the injection flow rate $Q_{pre}$ of the first solution and the blood flow rate $Q_B$, the substance A being absent from the first solution and the means for determining the infusion flow rate $Q_{post}$ comprising calculation means for calculating the infusion flow rate $Q_{post}$ according to the formula:

$$Q_{post} = \frac{(A)_{des} \times Q_B \times Q_{pre}}{(A)_{post} \times Q_B + (A)_{post} \times Q_{pre} - (A)_{des} \times Q_B}; \text{ and}$$

control means for governing the infusion means such that the flow rate of the second solution is substantially equal to the determined flow rate $Q_{post}$.

* * * * *

UNITED STATES PATENT AND TRADEMARK OFFICE
CERTIFICATE OF CORRECTION

PATENT NO. : 6,635,026 B1 Page 1 of 1
DATED : October 21, 2003
INVENTOR(S) : Bernard Béné

It is certified that error appears in the above-identified patent and that said Letters Patent is hereby corrected as shown below:

Title page,
Item [54], Title, "OF A LEAST" should read -- OF AT LEAST --.
Item [57], ABSTRACT,
Line 12, "a ionic" should read -- an ionic --.

Column 12,
Line 17, "into the a" should read -- into a --.

Signed and Sealed this

Third Day of February, 2004

JON W. DUDAS
*Acting Director of the United States Patent and Trademark Office*